United States Patent
Dozol et al.

[11] Patent Number: 6,156,282
[45] Date of Patent: Dec. 5, 2000

[54] CROWN CALIX[4]ARENES, METHOD OF PREPARATION AND USE FOR SELECTIVE EXTRACTION OF CAESIUM

[75] Inventors: Jean-François Dozol, Pierrevert; Véronique Lamare, Arxen Provence; Christophe Bressot, Paris, all of France; Rocco Ungaro; Alessandro Casnati, both of Parma, Italy; Jacques Vicens; Zouhair Asfari, both of Strasbourg, France

[73] Assignee: Commissariat a l'Energie Atomique, Paris, France

[21] Appl. No.: 09/171,525
[22] PCT Filed: Mar. 2, 1998
[86] PCT No.: PCT/FR98/00401
   § 371 Date: Jan. 27, 1999
   § 102(e) Date: Jan. 27, 1999
[87] PCT Pub. No.: WO98/39321
   PCT Pub. Date: Sep. 11, 1998

[30] Foreign Application Priority Data

Mar. 3, 1997 [FR] France .................. 97 02490

[51] Int. Cl.[7] .......................... C01D 15/00; B01D 11/00; C22B 26/10; C07D 321/00; C07D 321/10
[52] U.S. Cl. .................. 423/179; 423/181; 549/354; 540/468; 540/469; 540/472
[58] Field of Search .................. 423/179, 181; 549/348, 354; 540/468, 469, 472

[56] References Cited

U.S. PATENT DOCUMENTS 4,477,377  10/1984  Izatt et al. ................. 252/631
5,607,591   3/1997  Dozol et al. ............... 210/638

FOREIGN PATENT DOCUMENTS 2698362  11/1992  France .

OTHER PUBLICATIONS

Abstracts WO9424138 and EP695304.
Abstracts WO9412502, FR2698362 and EP670840.
Notification D'Un Rapport De Recherche Preliminaire Sans Reponse Obligatoire.

*Primary Examiner*—Steven P. Griffin
*Assistant Examiner*—Jonas N. Strickland
*Attorney, Agent, or Firm*—Burns Doane Swecker & Mathis L.L.P.

[57] ABSTRACT

The invention relates to new calixarenes of formula:

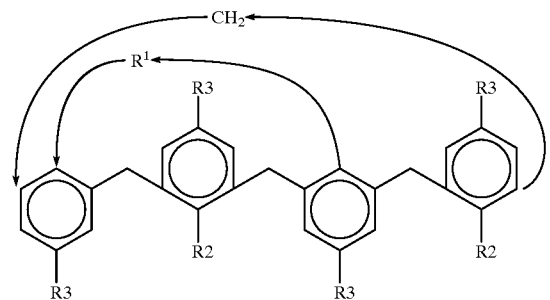

in which
  $R^1$ represents a crown ether chain that includes at least two aryl or cycloalkyl rings,
  $R^2$ is a hydroxyl or alkoxy group, or the two $R^2$ groups together form a crown ether chain such as $R^1$, and $R^3$ represents a hydrogen atom or an alkyl group. The calixarenes are used to selectively extract caesium from aqueous solutions that notably have high concentrations of sodium.

27 Claims, 7 Drawing Sheets

17

CROWN CALIX[4]ARENES, METHOD OF PREPARATION AND USE FOR SELECTIVE EXTRACTION OF CAESIUM

TECHNOLOGICAL FIELD

The subject of this invention is crown calix[4]arenes, their method of preparation and their use for the selective extraction of caesium.

To put it more precisely, the invention relates to crown calix[4]arenes capable of selectively extracting caesium present in trace amounts in acid solutions, that may or may not have high concentrations of cations, such as the aqueous effluents arising from spent nuclear fuel reprocessing plants.

In these effluents, caesium 137 is one of the most noxious fission products due to its long half-life (30 years). It is therefore of interest to selectively remove it from liquid effluents coming from reprocessing plants, in particular from evaporator concentrates and acid solutions that may or may not have high salinity due, in particular to the presence of sodium nitrate.

Given the great similarity of the chemical properties of sodium and caesium, it is extremely difficult to selectively extract the caesium present in these effluents, at a concentration generally lower than $10^{-6}$ mol/l, while the concentration of sodium is about 4 mol/l.

In acid solutions of fission products, it is equally important to remove the $^{135}$Cs with a half life of $2\times10^6$ years, with the intention either of transmuting it or incorporating it into a specified matrix, caesium being one of the most mobile elements in geological storage.

STATE OF THE PRIOR ART

In order to resolve this problem, it has been proposed to extract caesium using macrocyclic ligands such as the para tert-butyl-calixarenes described in U.S. Pat. No. 4,477,377. The para tert-butyl-calixarenes used are the tetramer, the hexamer and the octamer and the best results are obtained with the hexamer and the octamer, the tetramer not having very good selectivity for the separation of caesium from potassium. This technique for extracting caesium is interesting but its main disadvantage is that it is only applicable to aqueous basic solutions while most effluents arising from reprocessing are acid solutions.

More recently, for this separation the use of other calixarenes has been considered, in particular crown calixarenes as described in documents WO-A-94/12502 and WO-A-94/24138.

According to these documents, the one or two calixarene crowns are mainly made up of —$C_2H_4$—O— chains which comprise from 4 to 7 atoms of oxygen.

The results obtained with crowns with 6 or 7 atoms of oxygen are satisfactory for the extraction of caesium from acid solutions which are not highly loaded with salts. On the other hand, when they are used with effluents highly loaded with sodium, containing, for example 4 mol.l$^{-1}$ of NaNO$_3$, their performance is clearly reduced. Also research has been pursued to find other extraction agents of the same type having improved performance in highly saline acid media.

The precise objective of this invention is new crown calixarenes which allow the selective extraction of caesium from acid solutions and the separation of it from sodium with better efficiency.

DESCRIPTION OF THE INVENTION

According to the invention, the calixarenes are crown calix[4]arenes of formula:

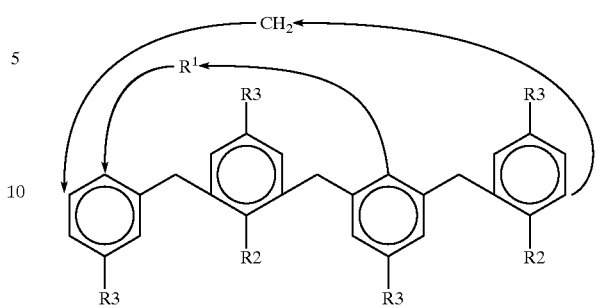

in which:

R$^1$ represents a group of formula:

where X and Y, which can be identical or different, represent an arylene or cycloalkylene group, m, n, p, r and s are whole numbers such that:

$m=s=1$, $1 \leq n \leq 3$, $p=0$ or $1$ $r=0$ or $1$,

R$^2$ represents an OH group or an alkoxy group with from 1 to 18 carbon atoms, the two R$^2$ groups can be identical or different, or the two R$^2$ groups together form a group of formula:

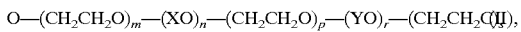

in which X, Y, m, n, p, r and s are as defined above; and

R$^3$ represents a hydrogen atom or an alkyl group with 1 to 3 carbon atoms, with the condition that, in the case where the two R$^2$ groups together form a group of formula (III), p and r will not both be equal to 0 when n=1.

In the formula given above, the alkoxy groups used for R$^2$ can be straight chain or branched chain and are not necessarily identical.

Generally, they comprise from 1 to 18 atoms of carbon, preferably from 1 to 12 atoms of carbon.

In the formula given above, by "cycloalkylene group" one understands a bivalent group derived from a cyclic hydrocarbon by the removal of a hydrogen atom from each of two carbon atoms in the ring. As an example of such a group, one may mention the cyclohexylene group. The cycloalkylene groups used for X and Y generally comprise from 6 to 14 atoms of carbon.

In this formula, by "arylene group", one understands a group derived from an aromatic hydrocarbon comprising one or more aromatic rings or a heterocyclic ring including a heteroatom such as O, S or N, by the removal of an atom of hydrogen from each of two carbon atoms in the ring.

As examples of such groups one may mention phenylene, naphthylene, benzylene, pyridylene and thienylene groups.

In the calixarenes of the invention, the presence of one or two crown ether chains R$^1$ that include from 2 to 6 cyclic groups, for example phenylene groups, confers on the molecule greater rigidity of the crown and improves its extractive properties and its selectivity with respect to caesium in relation to sodium, in particular in a highly saline medium as will be seen below.

According to a first embodiment of the invention, the crown calix[4]arene of formula (I) includes a single crown ether chain. In this case, the two $R^2$ groups of formula (I) represent an hydroxy group and an alkoxy group.

According to a second embodiment of the invention, the crown calix[4]arene of formula (I) includes two crown ether chains which are preferably identical. In this case, the two $R^2$ groups together form a group identical to $R^1$.

According to the invention the crown ether chain or chains represented by $R^1$ and corresponding to formulae II, IIa or IIb can include from 2 to 6 saturated cyclic or aryl groups. Generally it is preferable to use aryl groups such as phenylene groups.

Good results for the selective extraction of caesium are obtained when the crown calix[4]arene includes one or two crowns $R^1$ of formula:

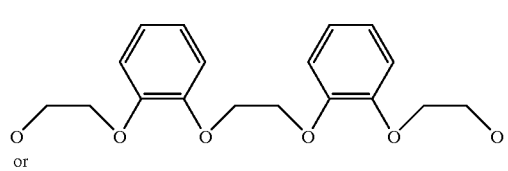

(III)

or

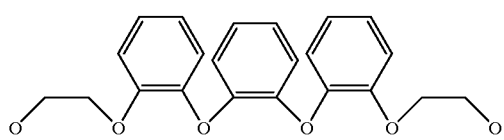

(IV)

Generally, in the calixarenes of the invention, $R^3$ represents an atom of hydrogen.

The crown calixarenes of formula (I) of the invention can be prepared from corresponding calixarenes by reaction with a ditosylate that includes the $R^1$ group.

Hence, the crown calixarenes with a single crown, corresponding to the first embodiment of the invention can be prepared by reaction of a calix[4]arene of formula:

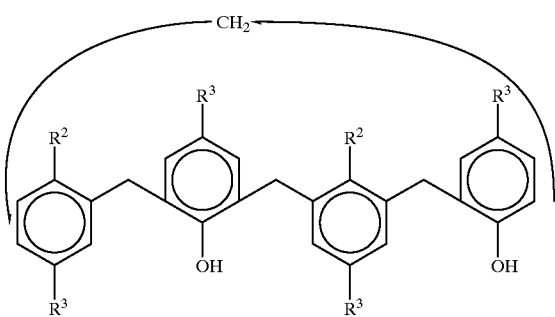

(V)

in which $R^2$ and $R^3$ are as stated above, with a ditosylate of formula (VI):

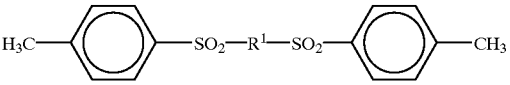

(VI)

in which $R^1$ is as stated above.

The crown calixarenes with two crowns corresponding to the second embodiment of the invention of formula (Ia):

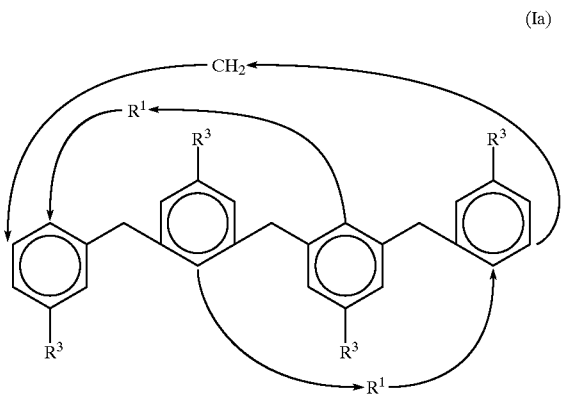

(Ia)

in which $R^1$ and $R^3$ are as defined above, can be prepared by reaction of a calix[4]arene of formula:

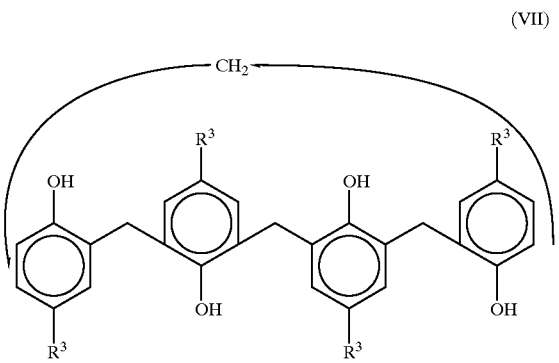

(VII)

with a ditosylate of formula:

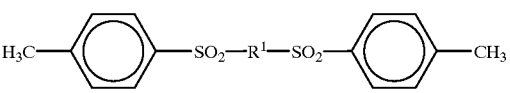

(VI)

in which $R^1$ is as stated above.

In order to carry out this reaction of forming the $R^1$ crown or crowns, the calixarene of formula (V) or (VII) is dissolved in a suitable solvent, for example, benzene or acetonitrile, a salt such as caesium carbonate and the ditosylate of formula (VI) are added, and the mixture is left to react under reflux for a period of time sufficient to form the $R^1$ crown or crowns by linking two benzene rings opposite one another. After reaction, the solvent is evaporated, the residue is taken up in hydrochloric acid and the product obtained is purified by the usual methods.

The calixarene of formula (V) used as starting product for the preparation of the single crown calix[4]arene can be prepared from the calix[4]arene of formula (VII) by reaction with a tosylate of formula:

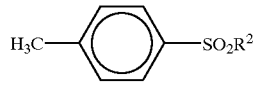
(VIII)

in which R² is as stated above.

The ditosylates of formula (VI) used as starting products for the preparation of the single crown and double crown calixarenes can be prepared by the usual methods from a diphenol such as catechol, or from a derivative of phenol in order to establish the O—CH₂—CH₂—O bonds or the

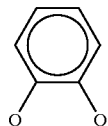

linkages of the $R^1$ chain.

Hence, for the case where $R^1$ represents the group of formula:

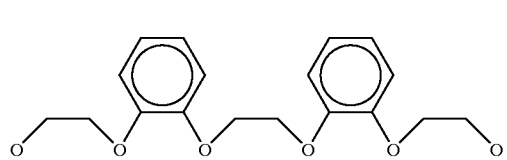
(III)

one can prepare the tosylate by carrying out the following steps:

a) synthesis of the 2-(2-hydroxyethoxy)phenol of formula:

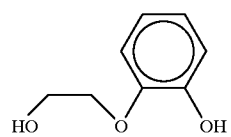
(IX)

by reaction of catechol with ethylene carbonate b) reaction of the 2-(2-hydroxyethoxy)phenol obtained in a) with ethylene glycol ditosylate to obtain 1,2-bis[2-(2-hydroxyethoxy)phenoxy]ethane, and c) preparation of the tosylate by reaction of the 1,2-bis[2-(2-hydroxyethoxy)phenoxy]ethane with tosyl chloride of formula:

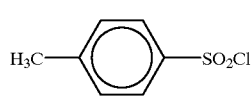
(X)

One can also prepare this tosylate by carrying out the following steps:

a) reaction of catechol with 2-chloroethanol to obtain 2-(2-hydroxyethoxy)phenol of formula:

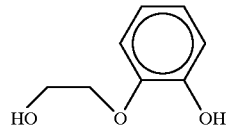
(IX)

b) reaction of the 2-(2-hydroxyethoxy)phenol obtained in a) with 1,2-dibromoethane to obtain 1,2-bis[2-(2-hydroxyethoxy)phenoxy]ethane and c) preparation of the tosylate by reaction of 1,2-bis[2-(2-hydroxyethoxy)phenoxy]ethane with tosyl chloride of formula (X):

(X)

In the case where $R^1$ represents the group with formula (IV), the tosylate can be prepared by carrying out the following steps:

a) preparation of the diphenol of formula:

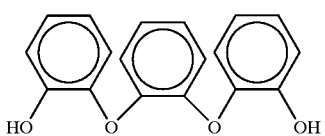
(XI)

b) reaction of the diphenol with ethylene glycol ditosylate.

This tosylate can also be prepared by carrying out the following steps:

a) preparation of the diphenol of formula:

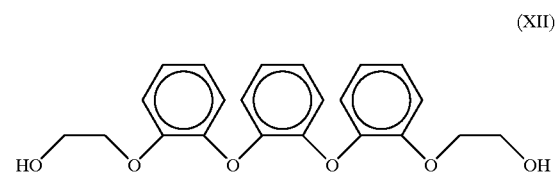
(XII)

b) reaction of the diphenol with tosyl chloride:

(X)

The crown calix[4]arenes of formula (I) previously described can be used, in particular for the selective extraction of caesium present in aqueous solutions, notably acid solutions loaded or not loaded with sodium such as dissolution solutions and aqueous effluents arising from spent nuclear fuel reprocessing plants.

For the extraction of caesium, the starting aqueous solutions can be acid solutions, for example nitric acid solutions containing from $10^{-3}$ to 7 mol/l nitric acid.

In order to carry out this extraction, the starting aqueous solution, called the first aqueous solution, containing the caesium is brought into contact with an immiscible liquid phase including the crown calix[4]arene, then the immiscible liquid phase is separated from the first aqueous solution.

The caesium can then be recovered in a second aqueous solution by bringing the immiscible liquid phase which has extracted the caesium into contact with a second aqueous re-extraction solution. The latter can be made up of distilled water and de-ionised water.

To implement this method, the first solution and the second solution can be contacted with the immiscible liquid phase using traditional extraction equipment such as mixer-decanters, pulsed columns etc.

This bringing into contact can also be carried out by arranging the immiscible liquid phase that includes the crown calix[4]arene as a liquid membrane comprising two opposite surfaces. The first starting aqueous solution containing the caesium is in contact with one of the surfaces of the membrane while the caesium extracted by the liquid membrane is recovered in the second aqueous re-extraction solution which is in contact with the other surface of the membrane.

To form the immiscible liquid phase, the crown calix[4]arene is dissolved in a suitable solvent.

By way of examples of solvents used, one can mention the alkyl benzenes and the nitrophenyl alkyl ethers.

Preferably, an ether such as ortho-nitrophenyl hexyl ether and ortho-nitrophenyl octyl ether is used as a solvent.

The concentration of the crown calix[4]arene in the immiscible liquid phase, depends, in particular on the solvent used. Concentrations ranging from $10^{-4}$ to $5 \times 10^{-1}$ mol/l can be used, for example a concentration of $10^{-2}$ mol/l.

According to the invention, the immiscible phase can also be a solid phase. In the case of a solid phase, this can be impregnated with one or more calixarenes of the invention, in the pure state or in solution in a suitable solvent. One can also use a solid phase onto which the calixarene or calixarenes of the invention are grafted.

In the case where one is using a solid immiscible phase, this can be made up of a solid support onto which the calixarene is fixed. This can be in the form of a supported liquid membrane made up of a microporous membrane playing the role of support, the pores of which are filled with calixarene in solution in a suitable organic solvent.

This microporous membrane can be produced in polypropylene, in polyvinylidene fluoride or in polytetrafluoroethylene, and it can be used as a separation between a first compartment in which there is the first aqueous solution which is to be treated and a second compartment in which there is the second aqueous re-extraction solution.

In order to obtain good extraction with the supported liquid membranes, it is advantageous to use membranes having low thickness, high porosity and a small pore diameter. These membranes can be used in the form of modules such as ultra modules or microfiltration modules with flat membranes or with hollow fibres which allow high fluid flow rates to be processed.

Other characteristics and advantages of the invention will be better apparent on reading the following examples given, it is understood for the purposes of illustration and which are non-limitative and make reference to the appended drawings.

DETAILED DESCRIPTION OF EMBODIMENTS

The examples which follow illustrate the preparation of calix[4]arenes conforming to the invention and their use for the extraction of caesium from acid aqueous solutions loaded or not loaded with salts.

Examples 1 and 2 illustrate the preparation of single crown calixarenes, and examples 3 and 4 illustrate the preparation of bis-crown calixarenes.

EXAMPLE 1

Preparation of 25,27-dioctyloxy-calix[4]arene-dibenzo-crown-6 (compound 7)

This calixarene corresponds to formula (I) of the invention with $R^1$ representing the group with formula (III), the two $R^2$ groups representing the octoxy group and the $R^3$ groups being an atom of hydrogen.

Figure 1A:
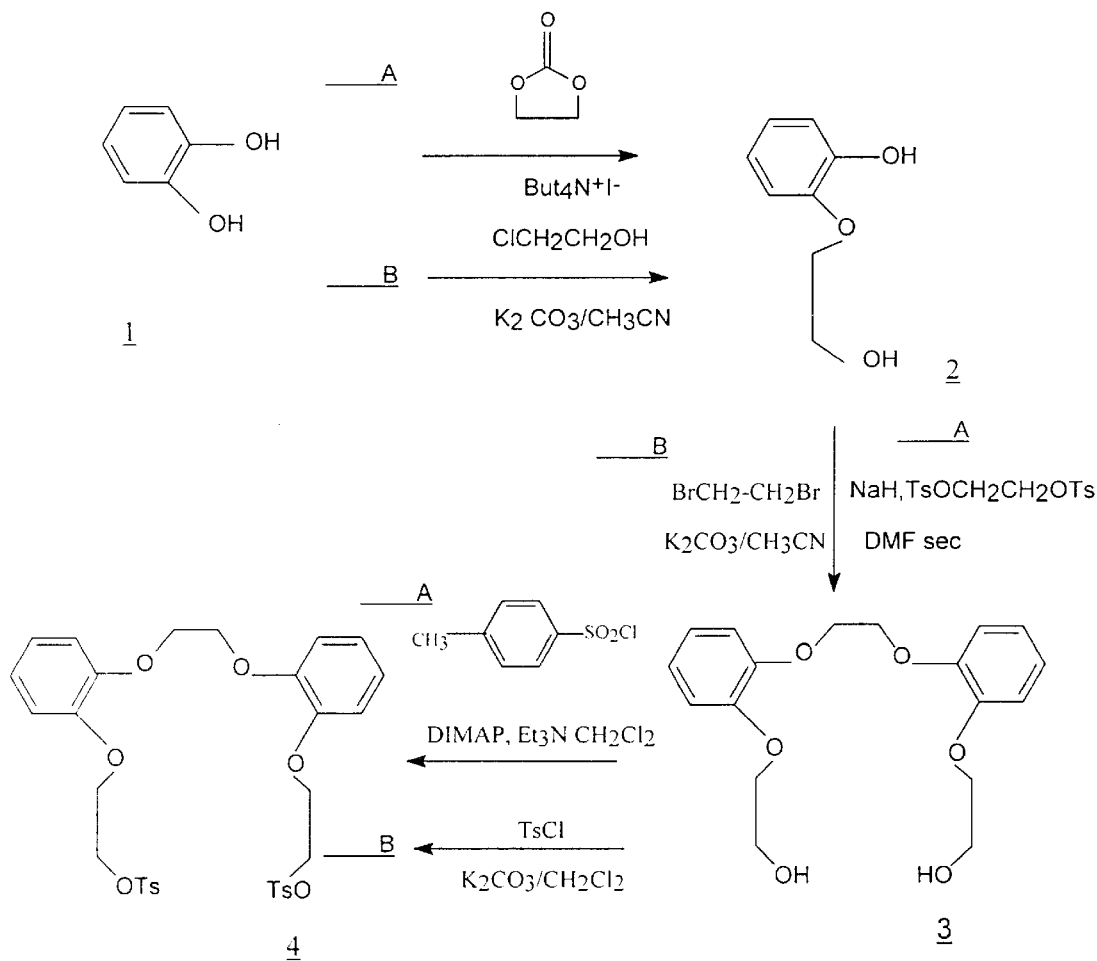
FIG. 1 (1A and 1B) illustrates two synthesis diagrams for calixarenes conforming to the invention. In this figure, route A corresponds to a single crown calixarene and route B to a double crown calixarene.
Figure 1B:
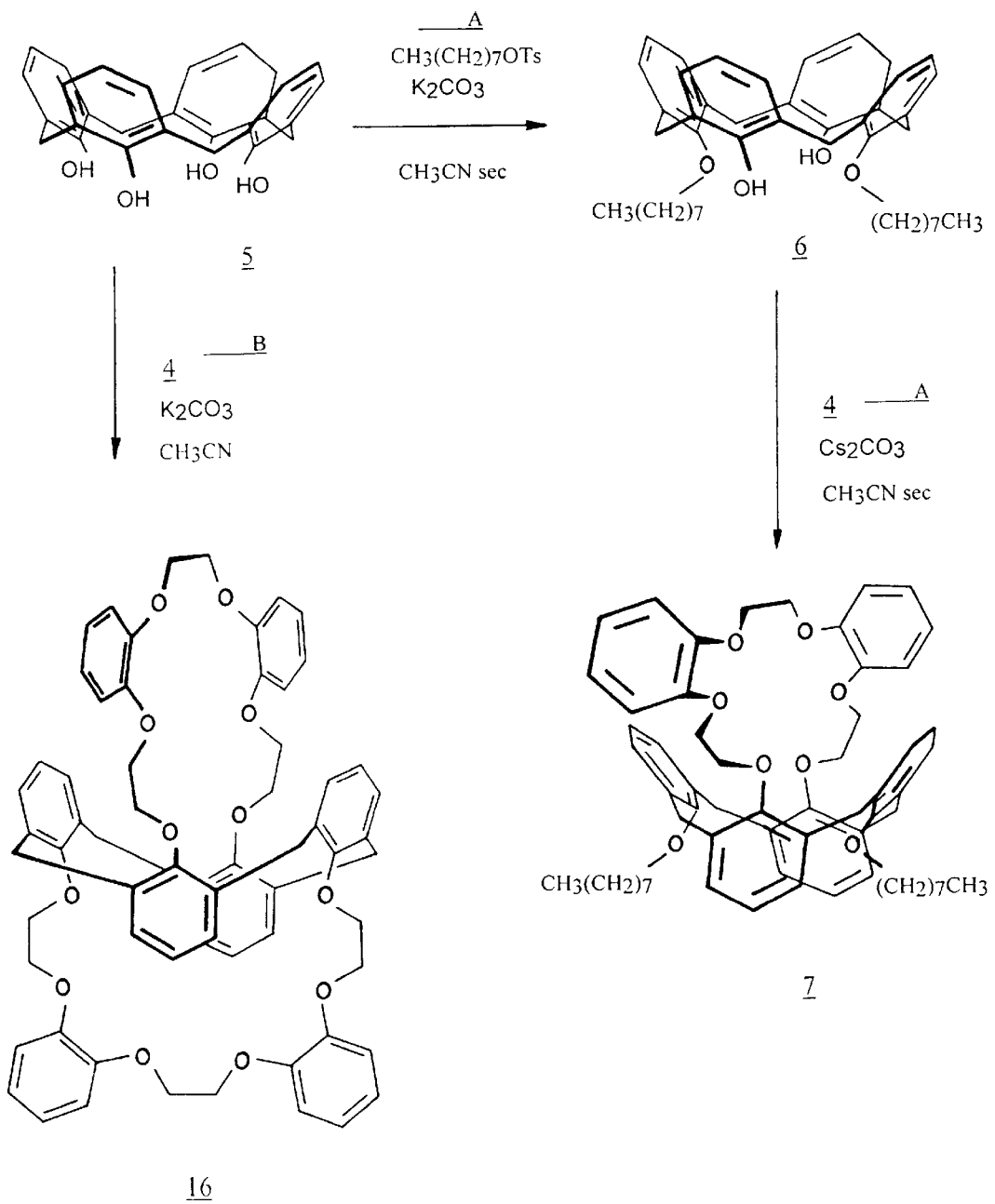

This synthesis is carried out in accordance with the reaction diagram illustrated in FIG. 1 (route A).

Steps a) and b) below use a synthesis method adapted from Yamaguchi, K., Negi, S., Kozaki, S., Nagano, R., Kuboniwa, H., Hirao, A., Nakahama, S., Yamazaki, N., *Bull. Chem. Soc. Jpn.*; 61, 2047–2054, 1988.

a) Synthesis of 2-(2-hydroxyethoxy)phenol (compound 2)

A mixture of catechol 1 (22 g, 0.2 mol), ethylene carbonate (17.6 g, 0.2 mol) and tetrabutyl ammonium iodide (2.4 g, 6.5 mol) is heated to 160° C. for about 1 hour until the release of $CO_2$ stops.

The mixture is purified by chromatography on a silica column using a (1:1) mixture of hexane and ethyl acetate as eluent and one obtains a white solid. 4.1 g of pure compound 2 is obtained by recrystallisation in water, which corresponds to a yield of 46%.

The characteristics of compound 2 are as follows:

Melting point: 100–101° C.

$^1$H NMR (CDCl$_3$)δ(ppm): 6.95–6.80(m, 5H, ArO$\underline{H}$ and ArH), 4.13–4.10 (m, 2H, ArOC$\underline{H}_2$), 4.0–3.97 (m, 3H, OCH$_2$C$\underline{H}_2$O$\underline{H}$). Mass spectrometry(IC): m/e=155 (M$^+$).

b) Synthesis of 1,2-bis[2-(2-hydroxyethoxy)-phenoxy]-ethane (compound 3)

A mixture of compound 2 (2 g, 13 mmol) and NaH (0.32 g, 13 mmol) in 8 ml of dry dimethylformamide (DMF) is stirred for 30 minutes at ambient temperature. Ethylene glycol ditosylate (2.4 g, 6.4 mmol) dissolved in 25 ml of dry DMF is added drop by drop to this solution and the mixture is stirred at ambient temperature for 36 hours. After removing the DMF under vacuum, the residue is dissolved in dichloromethane and this is washed with water. The organic layer, dried over sodium sulphate is evaporated. 1.71 g of pure compound 3 is obtained by recrystallisation from a ethanol-water mixture (1:1), which corresponds to a yield of 81%.

The characteristics of this compound are as follows:

M. Pt.: 75–77° C.

$^1$H NMR (CDCl$_3$)δ(ppm): 6.97–6.89(m, 8H, ArH), 4.39 (s, 4H, ArOC$\underline{H}_2$C$\underline{H}_2$OAr), 4.34 (s, 2H, OH), 4.1 (t, J=7 Hz, 4H, ArOC$\underline{H}_2$CH$_2$OH), 3.87 (t, J=7 Hz, 4H, ArOCH$_2$C$\underline{H}_2$OH).

Mass spectrometry(IC): m/e=335 (M$^+$).

c) Synthesis of 1,2-bis[2-(2-hydroxyethoxy)-phenoxy]-ethane, bis(p-toluenesulphonate) (compound 4)

For this synthesis, a method adapted from Weber, E., J. Org. Chem.; 47, 1982, pages 3478–3486 is used.

A mixture of compound 3 (2 g, 5.9 mmol) and triethylamine (1.7 ml, 12 mmol) in 32 ml of dichloromethane is cooled to 0° C. Tosyl chloride (2.3 g, 12 mmol) and 4-dimethylaminopyridine (7.3 mg, 0.06 mmol) is added to this solution.

After 3 hours, the mixture is extracted with 50 ml of 10% HCl. The organic layer is dried over sodium sulphate and evaporated under vacuum. 2.3 g of pure compound 4 is obtained by recrystallisation from methanol, which corresponds to a yield of 60%. The characteristics of this compound are as follows:

M. Pt.: 91–93° C.

$^1$H NMR (CDCl$_3$)δ(ppm): 7.75(d, J=8 Hz, 2H, $\underline{Ar}$OCH$_3$), 7.27 (d, J=8, 2H, $\underline{Ar}$CH$_3$), 6.86–6.81 (m, 8H, ArH), 4.34 (s, 4H, ArOC$\underline{H}_2$C$\underline{H}_2$OAr), 4.19–4.16 (m, 8H, TsOC$\underline{H}_2$C$\underline{H}_2$O), 2.39 (s, 6H, CH$_3$Ar).

Mass spectrometry(IC): m/e=642 (M$^+$)

d) Synthesis of compound 7

A solution of calix[4]arene 5 (1.0 g, 2.36 mmol) and potassium carbonate (0.48 g, 3.53 mmol) in 15 ml of dry acetonitrile is refluxed under an atmosphere of nitrogen for 30 minutes.

After adding octyl tosylate (2.01 g, 7.07 mmol), the mixture is refluxed for 48 hours. Then the acetonitrile is removed under reduced pressure and the residue treated with 50 ml of 10% HCl and 50 ml of dichloromethane. The organic layer is separated, washed twice with distilled water, dried over magnesium sulphate and then the dichloromethane is removed by distillation. Ethanol is then added and the precipitate is separated by filtration. 1.3 g of a white solid is obtained (yield of 85%) corresponding to 25,27-di-octoxy calix[4]arene 6.

It is dried under forced vacuum for several hours and dissolved in 310 ml of acetonitrile. An excess of caesium carbonate (2.64 g, 8.1 mmol) and the compound 4 (1.3 g, 2.02 mmol) is added under an atmosphere of nitrogen. The reaction mixture is refluxed for 16 hours and then treated with 10% HCl. Washing and separation are carried at as in the case of compound 6.

In this way 1.07 g of compound 7, 25,27-di-octoxycalix[4]arene-dibenzo-crown-6 is obtained, (a yield of 56%) from the oily residue by chromatography on a silica column using a mixture of tetrahydrofurane THF and hexane (1:9) as eluent and by crystallisation from methanol.

The characteristics of compound 7 are as follows:

M. Pt=130° C.

$^1$H NMR (CDCl$_3$)δ(ppm): 7.10–6.99 (m, 12H, ArH), 6.80 (t, J=6.5 Hz, 2H, ArH para), 6.78 (d, J=6.5 Hz, 4H, ArH meta), 6.58 (t, J=6.5 Hz, 2H, ArH para), 4.37 (s, 4H, ArOC$\underline{H}_2$C$\underline{H}_2$OAr), 3.77 (s, 8H, ArCH$_2$Ar), 3.63 (t, J=6 Hz, 4H, ArOC$\underline{H}_2$CH$_2$OArO), 3.47 (t, J=6 Hz, 4H, ArOCH$_2$C$\underline{H}_2$OArO), 3.36 (t, J=6 Hz, 4H, ArOCH$_2$R), 1.36–1.1 (m, 24H, OCH$_2$(C$\underline{H}_2$)$_6$CH$_3$), 0.92 (t, J=6.5 Hz, 6H, —CH$_3$)

Mass spectrometry (IC): m/e=948 (M$^+$)

EXAMPLE 2

Synthesis of 1,3-dioctoxy calix[4]arene-tribenzo-crown-6 (compound 15).

This compound corresponds to formula (I) of the invention with R$^1$ representing the group with formula (IV), the two R$^2$ groups representing the octoxy group and R$^3$ representing an atom of hydrogen.

Figure 2A:
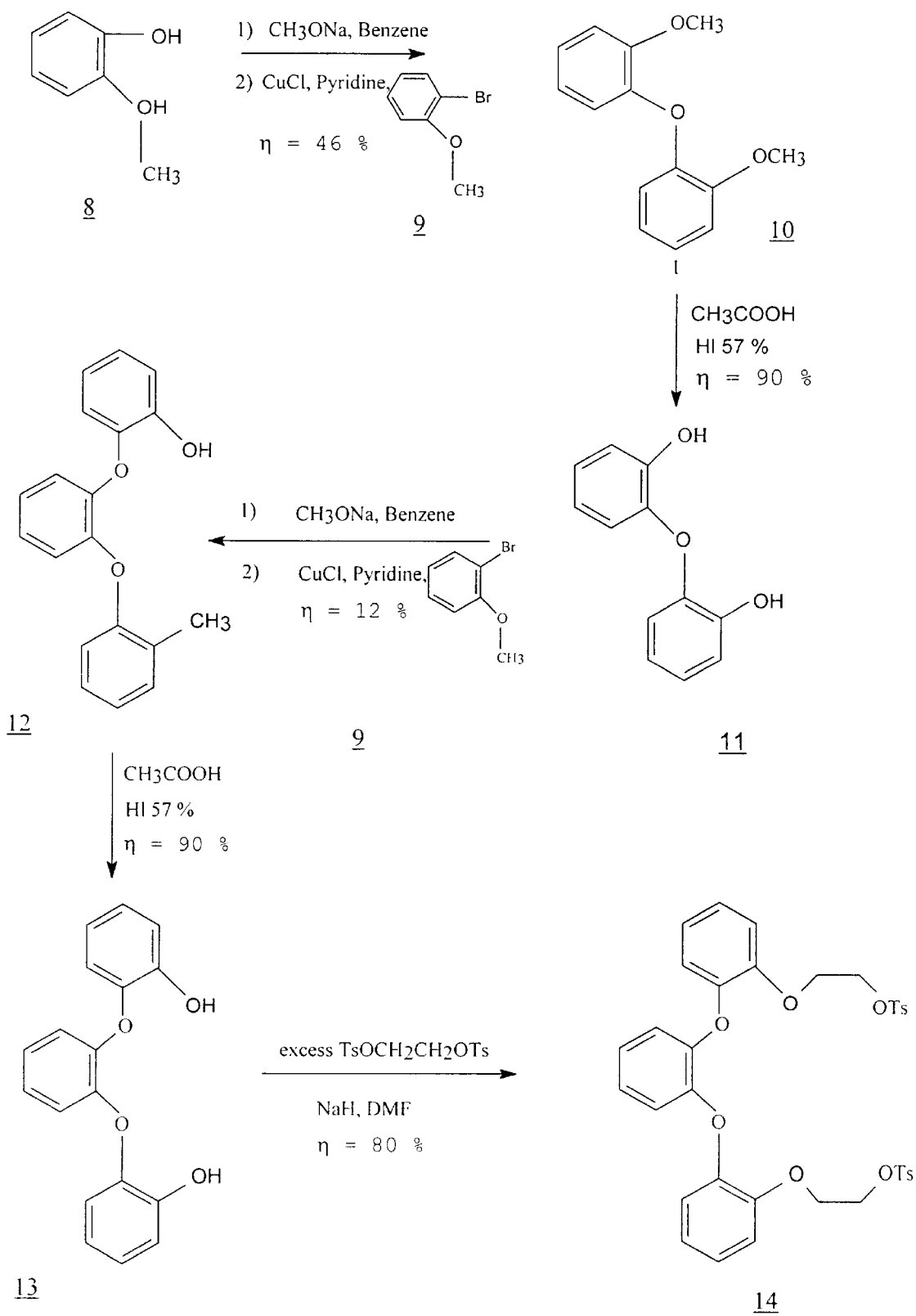
FIG. 2 (2A and 2B) illustrates the synthesis diagram for another single crown calixarene conforming to the invention.
Figure 2B:
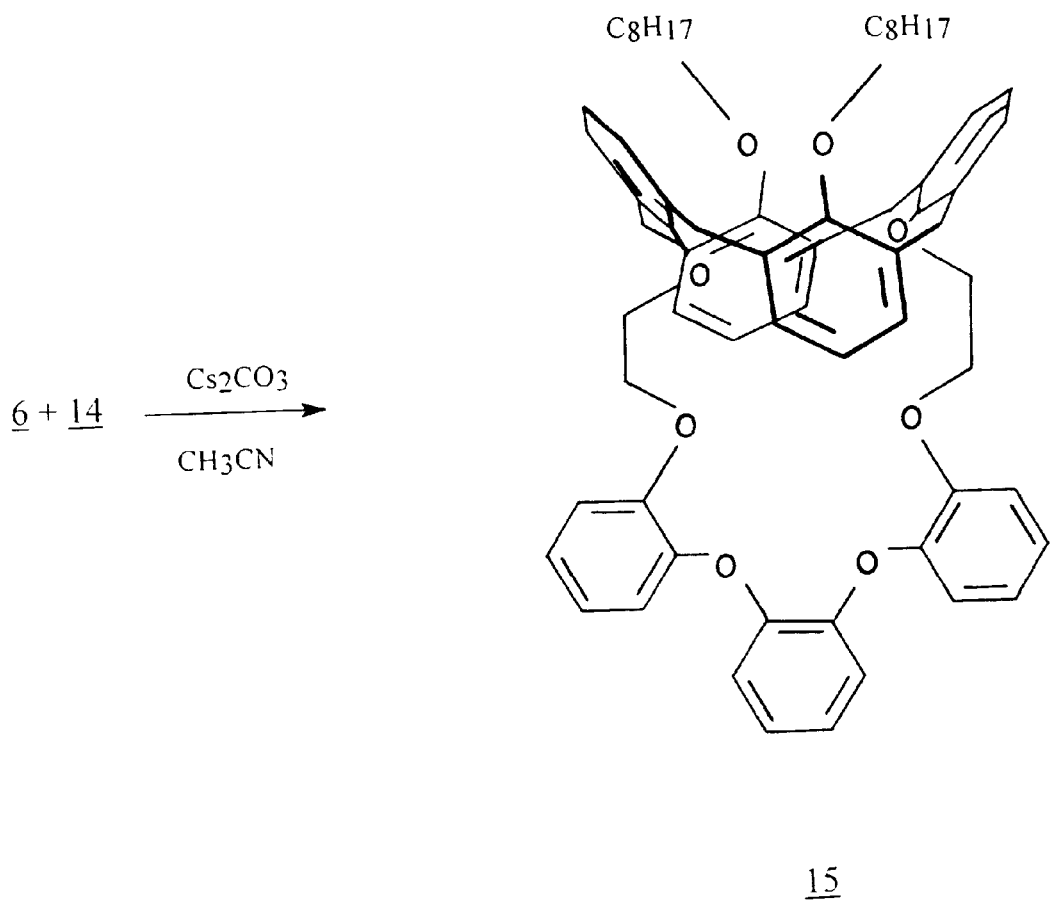

This synthesis corresponds to the diagram illustrated in FIG. 2.

For this synthesis, the same method is followed as in Example 1, reacting as in step d) of Example 1, the ditosylate 14 corresponding to the group R$^1$ of formula (IV) with the compound 6, or 25,27-dioctoxy calix[4]arene.

The ditosylate is obtained as shown in the synthesis diagram illustrated in FIG. 2. This synthesis is carried out following the method described by D. E. Kime, J. K. Norymbersky, J. Chem. Soc. Perkin Trans. 1, 1977, page 1048, to prepare compound 13.

Compound 13 is then treated with an excess of ethylene glycol di-p-toluene sulphonate in dry DMF with sodium hydride for 8 hours. The DMF is removed under reduced pressure and compound 14 is purified by column chromatography.

Subsequently, this compound 14 is reacted with the calix[4]arene 6 from Example 1 following the same method of operation as in Example 1.

The characteristics of compound 15 obtained in this way are as follows:

$^1$H NMR (CDCl$_3$)δ(ppm): 7.22–6.75 (m, 24H, ArH), 3.78 (s, 8H, ArCH$_2$Ar), 3.65 (t, J=6 Hz, ArOC$\underline{H}_2$CH$_2$OAr), 3.43 (t, J=6 Hz, ArOCH$_2$C$\underline{H}_2$OAr), 3.36 (t, J=6 Hz, 4H, ArOC$\underline{H}_2$(CH$_2$)$_6$CH$_3$), 1.3–1.1 (m, 24H, OCH$_2$(C$\underline{H}_2$)$_6$CH$_3$), 0.90 (t, J=6.5 Hz, 6H OCH$_2$(CH$_2$)$_6$C$\underline{H}_3$).

Mass spectrometry (IC): m/e=994.5 (M$^+$).

EXAMPLE 3

Synthesis of calix[4]arene-bis-dibenzo-crown-6, compound 16.

This compound corresponds to formula (I) of the invention with R$^1$ representing the group with formula (III), the two R$^2$ groups forming together the group with formula (III) and R$^3$ representing an atom of hydrogen.

For this synthesis, the reaction diagram shown in FIG. 1, route B, is followed. Hence one starts with catechol, compound 1, used as starting product in Example 1 and one converts it into compound 2, then into compound 3 and into compound 4 by working in a way that is only slightly different. Subsequently calix[4]-bis-crown is prepared by reaction of compound 4 with compound 5.

a) Preparation of compound 2

33.03 g (300 mmol) of catechol 1, 24.15 g (300 mmol) of 2-chloroethanol, 20.75 g (150 mmol) of K$_2$CO$_3$ and 750 ml of acetonitrile are put into a 1 l flask. The reaction mixture is refluxed for 48 hours. It is then allowed to return to ambient temperature, the solution is filtered and is concentrated. After purification by column chromatography (CHCl$_3$/acetone: 80/20), compound 2 is recovered in the form of a white solid (18.5 g); a yield of 40%.

NMR $^1$H spectrum in CDCl$_3$ at 200 MHz, δ in ppm

δ=6.99 to 6.78 (m, 4H, Ar)

δ=4.16 to 4.11 (m, 2H, OC$\underline{H}_2$CH$_2$)

δ=4.03 to 3.98 (m, 2H, OCH$_2$C$\underline{H}_2$OH)

δ=2.79 (s, broad, 2H, OH).

b) Preparation of compound 3

7.71 g (50 mmol) of compound 2, 69.1 g (500 mmol) of K$_2$CO$_3$, 5.64 g (30 mmol) of 1,2 dibromoethane and 750 ml of CH$_3$CN are put into a 1000 ml flask. The reaction mixture is refluxed for 4 days. After having allowed it to return to ambient temperature, the solvent is evaporated to dryness. The residue thus obtained is dissolved in $CH_2Cl_2$ and the $K_2CO_3$ neutralised with 1N HCl. The organic phase is dried over sodium sulphate and then concentrated. After purification by column chromatography ($CH_2Cl_2$/acetone: 85/15), compound 3 is recovered in the form of a white solid (4.2 g).

Yield: 25%

NMR $^1$H spectrum in $CDCl_3$ at 200 MHz, δ in ppm

δ=6.97 (s, 8H, Ar)

δ=4.40 to 4.34 (m, 6H, $OCH_2CH_2O$ and OH)

δ=4.14 to 4.10 (m, 4H, $OCH_2CH_2$)

δ=3.89 to 3.86 (m, 4H $OCH_2CH_2$).

c) Preparation of compound 4

2.0 g (6 mmol) of compound 3, 2.3 g (12 mmol) of tosyl chloride and 70 ml of dichloroethane are put into a 100 ml two necked flask. The reaction mixture is placed in an ice bath at 0° C. and then 2.3 g (22 mmol) of triethylamine is added drop by drop. After 48 hours of reaction at ambient temperature, the triethylamine is neutralised with a solution of 1N HCl. The organic phase is dried over sodium sulphate and then concentrated to give a beige solid. After purification by column chromatography ($CH_2Cl_2$/acetone: 95/5), the ditosylated product is recovered in the form of a white solid (2.4 g).

Yield: 62%

NMR $^1$H spectrum in $CDCl_3$ at 200 MHz, δ in ppm

δ=7.77 (d, 4H, J=8.5 Hz, system AB OTS)

δ=7.28 (d, 4H, J=8.5 Hz, system AB OTS)

δ=6.97 to 6.81 (m, 8H, Ar)

δ=4.31 to 4.27 (m, 8H, $OCH_2CH_2O$)

δ=4.20 to 4.16 (m, 4H, $OCH_2CH_2O$)

δ=2.40 (s, 6H, $ArCH_3$)

d) Preparation of compound 16

0.425 g (1 mmol) of calix[4]arene (compound 5) and 1.380 g (10 mmol) of $K_2CO_3$ in 100 ml of $CH_3CN$ were put into a 250 ml flask. The mixture was stirred for 4 hours at ambient temperature, then 0.643 g (1 mmol) of ditosylate 4 is added and the mixture heated under reflux for 7 days. The same quantity of $K_2CO_3$ and ditosylate is once again added to the solution and the reaction mixture is refluxed for 7 more days. After 14 days of reflux, the solvent is evaporated to dryness. The residue obtained is dissolved in dichloromethane and the $K_2CO_3$ neutralised with 1N HCl. The organic phase is dried over sodium sulphate and then concentrated. After purification by column chromatography ($CH_2Cl_2$/acetone: 90/10), the compound 16 dibenzo-bis-crown-6 is recovered in the form of a white solid (850 mg).

Yield: 83%

NMR $^1$H spectrum in $CDCl_3$ at 200 MHz, δ in ppm

δ=7.14 to 7.08 (m, 8H, Ar)

δ=6.96 to 6.89 (m, 8H, Ar)

δ=6.72 (d, 8H, J=7 Hz, H meta to the Ar)

δ=6.58 (d, 8H, J=7 Hz, H para to the Ar)

δ=4.39 (s, 8H, $OCH_2CH_2O$)

δ=3.74 (s, 8H, $ArCH_2$—Ar)

δ=3.49 (m, 16H, $OCH_2CH_2O$)

Mass spectrum FAB positive m/z=1021.5 (100%)

EXAMPLE 4

Synthesis of calix[4]arene-bis-crown-6 (compound 17).

This calixarene corresponds to formula (I) of the invention with $R^1$ representing the group with formula (IV), the two $R^2$ groups together forming the same group with formula (IV) and $R^3$ representing an atom of hydrogen.

Figure 3A:
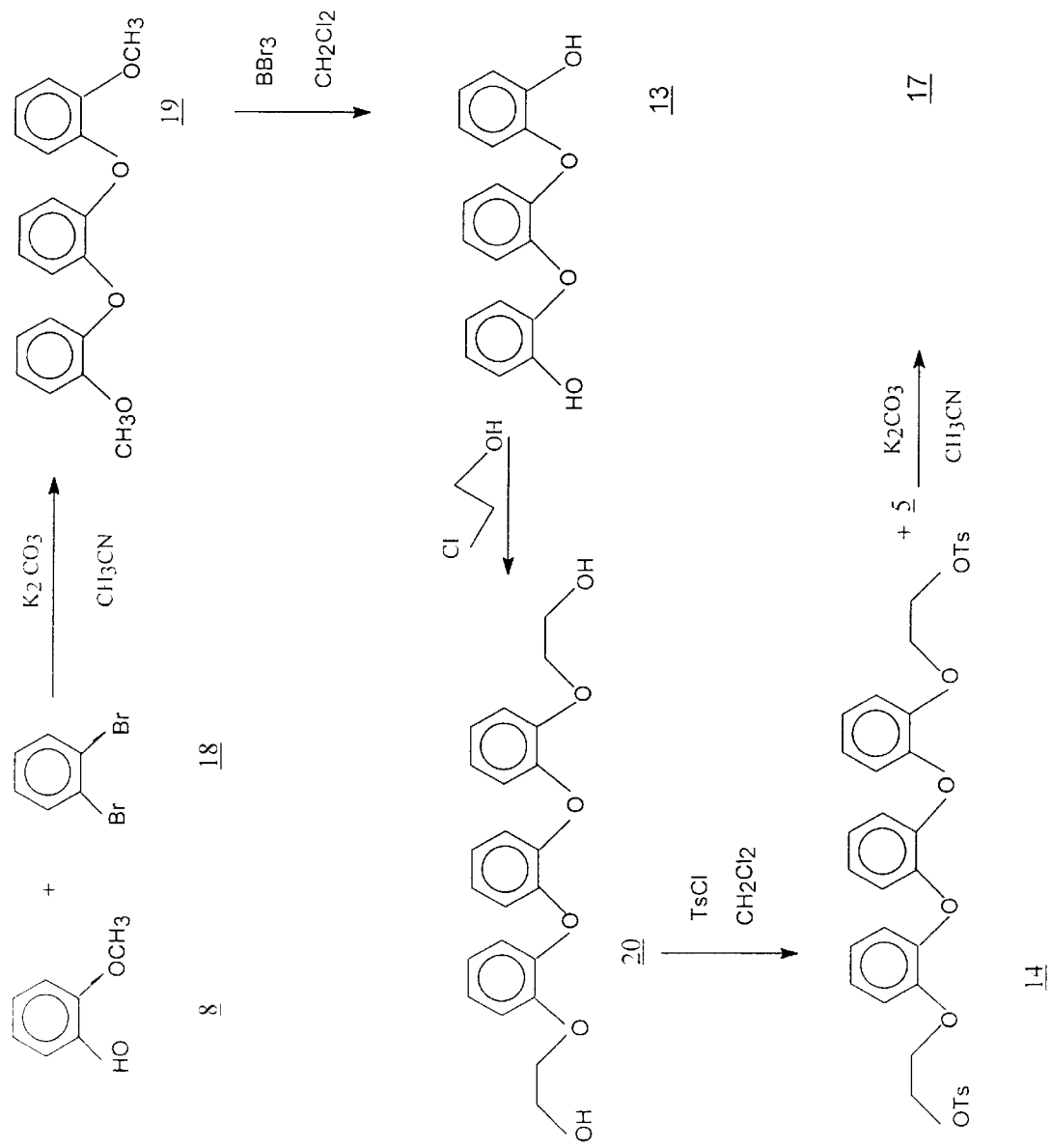
FIG. 3 (3A and 3B) illustrates the synthesis diagram for another double crown calixarene conforming to the invention.
Figure 3B:
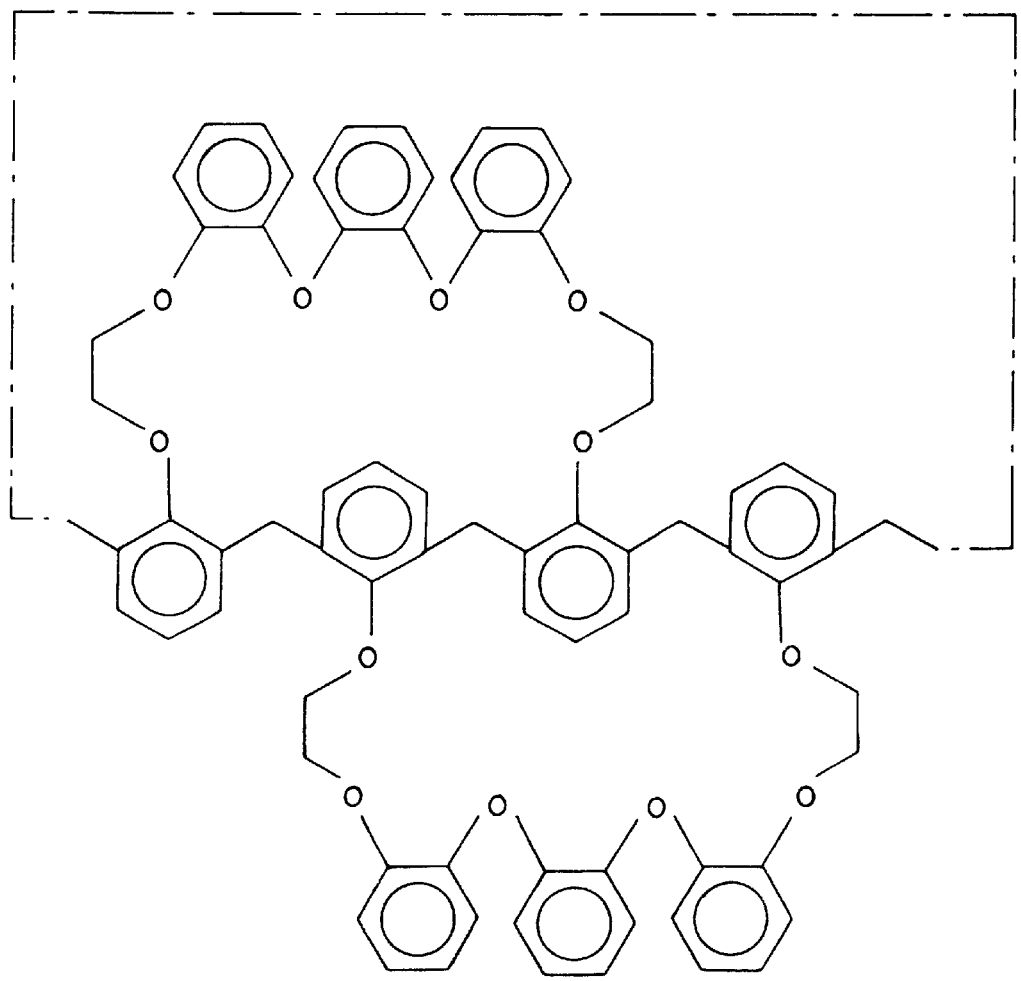

For this synthesis, the synthesis diagram given in FIG. 3 is followed. First the ditosylate is prepared from compound 8 used in Example 2, but by carrying out slightly different steps.

a) Preparation of compound 19

4.47 g (36 mmol) of Guaiacol 8 or 2-methoxyphenol, 24.88 g (180 mmol) of $K_2CO_3$ and 350 ml of acetonitrile are put into a 500 ml flask. After having stirred the solution for 2 hours at ambient temperature, 4.25 g (18 mmol) of 1,2-dibromobenzene 18 is added drop by drop and the reaction mixture heated under reflux for 4 days. After having allowed the reaction mixture to return to ambient temperature, the solvent is evaporated to dryness. The residue thus obtained is dissolved in dichloromethane and the $K_2CO_3$ neutralised with 1N HCl. The organic phase is dried over sodium sulphate, then concentrated. After purification by column chromatography ($CH_2Cl_2$), the product is recovered in the form of a yellow solid (3.45 g).

Yield: 30%

NMR $^1$H spectrum in $CDCl_3$ at 200 MHz, δ in ppm

δ=6.95 to 6.85 (m, 12H, Ar)

δ=3.89 (s, 6H, $CH_3$).

b) Preparation of compound 13

10 g (40 mmol) of boron tribromide $BBr_3$ and 300 ml of dichloromethane is put into a 500 ml two necked flask. After having stirred the solution for 30 minutes at −60° C., 3.22 g (10 mmol) of 2,2-[1,2-phenylenedi(oxy) diphenyl dimethyl ether] 19 is added drop by drop while maintaining the temperature at −60° C. After 10 hours of reaction, the excess $BBr_3$ is destroyed by adding methanol. The residue obtained is evaporated to dryness, then dissolved in dichloromethane. The organic phase is washed with a 5% $NaHCO_3$ solution, then dried over $Na_2SO_4$ and concentrated. A white solid is recovered by recrystallisation in n-heptane (2.6 g).

Yield: 88%

NMR $^1$H spectrum in $CDCl_3$ at 200 MHz, δ in ppm

δ=6.97 to 6.88 (m, 12H, Ar)

δ=6.58 (s, 2H, $CH_3$).

c) Preparation of compound 20

2.35 g (8 mmol) of 2,2'-[1,2-phenylenedi(oxy)diphenol] 13, 2.58 g (32 mmol) of 2-chloroethanol, 11 g (80 mmol) of $K_2CO_3$ and 200 ml of acetonitrile are put into a 500 ml flask. The reaction mixture is refluxed for 3 days. After having allowed it to return to ambient temperature, it is evaporated to dryness. The residue obtained is dissolved in dichloromethane and the $K_2CO_3$ neutralised with 1 N hydrochloric acid HCl. The organic phase is dried over sodium sulphate and then concentrated. After purification by column chromatography ($CH_2Cl_2$: acetone −90:10), the product 20 is recovered in the form of a white solid (1.9 g)

Yield: 62%

NMR $^1$H spectrum in $CDCl_3$ at 200 MHz, δ in ppm

δ=6.87 to 6.74 (m, 12H, Ar)

δ=4.32 (s, broad, 2H, OH)

δ=4.07 to 4.02 (m, 4H, $OCH_2CH_2$)

δ=3.74 to 3.69 (m, 4H, $OCH_2CH_2$)

d) Preparation of the ditosylate 14

1.8 g (4.7 mmol) of diethylene glycol triphenol 20, 1.8 g (9.4 mmol) of tosyl chloride and 60 ml of dichloroethane were put into a 100 ml two necked flask.

The reaction mixture is placed in an ice bath at 0° C. and then 2.3 g (22 mmol) of triethylamine is added drop by drop. After 48 hours reaction at ambient temperature, the triethylamine is neutralised with a 1N solution of hydrochloric acid HCl. The organic phase is dried over sodium sulphate and then concentrated to give a solid. After purification by column chromatography ($CH_2Cl_2$: acetone–98:2), the ditosylated product 14 is recovered in the form of a white solid (1.95 g).

Yield: 60%

NMR $^1H$ spectrum in $CDCl_3$ at 200 MHz, δ in ppm

δ=7.84 (d, 4H, J=8.5 Hz, system AB OTS)

δ=7.37 (d, 4H, J=8.5 Hz, system AB OTS)

δ=6.89 to 6.78 (m, 12H, Ar)

δ=4.22 to 4.18 (m, 4H, $OCH_2CH_2$)

δ=3.89 to 3.82 (m, 4H, $OCH_2CH_2$)

δ=2.39 (s, 6H, $ArCH_3$)

e) Preparation of calixarene-bis-crown 17

0.425 g (1 mmol) of calix[4]arene 5, 1.380 g (10 mmol) of $K_2CO_3$ in 100 ml of $CH_3CN$ is put into a 250 ml flask. The mixture is stirred for 4 hours at ambient temperature and then 0.691 g (1 mmol) of ditosylate 14 is added and the mixture heated under reflux for 7 days. The same quantity of $K_2CO_3$ 1.38 g (10 mmol) and ditosylate 0.691 g (1 mmol) is once again added to the solution and the reaction mixture is refluxed for 7 more days. After 14 days of reflux, the solvent is evaporated to dryness. The residue obtained is dissolved in dichloromethane and the $K_2CO_3$ neutralised with 1N HCl. The organic phase is dried over sodium sulphate and then concentrated. After purification by column chromatography ($CH_2Cl_2$/acetone: 90/10), the product tribenzo-bis-crown 17 is recovered in the form of a white solid (340 mg).

Yield : 30%

NMR $^1H$ spectrum in $CDCl_3$ at 200 MHz, δ in ppm

δ=7.22 to 6.94 (m, 24H, Ar)

δ=6.69 (d, 8H, J=7 Hz, H meta to the Ar)

δ=6.55 (t, 4H, J=7 Hz, H para to the Ar)

δ=3.72 (s, 8H, Ar—$CH_2Ar$)

δ=3.21 to 3.17 (m, 16H, $OCH_2CH_2O$)

The examples which follow illustrate how the calixarenes of the invention are used for the selective extraction of caesium.

EXAMPLE 5

Extraction of caesium

In this example, using calixarenes of the invention, caesium is extracted from an aqueous solution having a nitric acid concentration of 1 mol/l and containing $5 \times 10^{-4}$ mol/l of $CsNO_3$.

For this purpose, a volume of aqueous solution is brought into contact with a volume of organic liquid constituted by ortho-nitrophenyl hexyl ether containing $10^{-2}$ mol/l of calixarene. When equilibrium is reached, the caesium content of the organic liquid is measured by gamma spectrometry. Then the percentage caesium extracted is determined and the distribution coefficient DCS which corresponds to the ratio of the concentration of caesium in the organic liquid to the concentration of caesium in the aqueous solution at equilibrium.

For these experiments, the calixarenes from Examples 1 and 3 above were used. The results obtained are given in Table 1.

For comparison purposes, in Table 1, the results are also given that were obtained under the same conditions with calixarenes of the prior art, which are the calixarenes from Examples 3 and 6b in the document WO94/12502 and the calixarene bis-1,2-naphtho crown-6 and the single crown calixarenes of Examples 3, 4 and 6 in document WO94/24138.

EXAMPLE 6

Extraction of sodium

In this example, one starts with an aqueous solution having a nitric acid concentration of 1 mol/l, containing $5 \times 10^{-4}$ mol/l of sodium nitrate. It is subjected to an extraction under the same conditions as those in Example 5, using a calixarene at a concentration of $10^{-2}$ mol/l in ortho-nitrophenyl hexyl ether. As previously the sodium content of the organic solution is measured by gamma spectrometry and the percentage of sodium extracted and the distribution coefficient $D_{na}$ are calculated.

The same calixarenes are used as in Example 5. The results obtained are given in Table 1.

EXAMPLE 7

Extraction of caesium

The same method of operation as in Example 5 is followed to extract the caesium from an aqueous solution of a composition different to that of Example 1, and which contains:

1 mol/l nitric acid 4 mol/l sodium nitrate, and $5 \times 10^{-4}$ mol/l $CsNO_3$ The calixarenes and the solvent used are the same as those in Example 1.

The results obtained are given in Table 1.

The results in Table 1 show that the single crown and bis-crown calix[4]arenes of the invention extract caesium with good yields and separate it from the sodium also present in the effluents coming from reprocessing plants. Furthermore, they show that in the presence of high concentrations of sodium, the calixarenes of the invention permit selective extraction of much greater quantities of caesium while the opposite occurs with the calixarenes of the prior art.

In effect, Dc, increases from 31 to 56 or from 23 to 54 with the calixarenes of the invention while $D_{Cs}$ decreases in all cases with the calixarenes of the prior art.

Therefore, with the calixarenes of the invention, a surprising effect on the extraction of caesium is obtained.

EXAMPLE 8

Transport of the caesium

In this example, the extraction of caesium-137 is carried out in the presence of sodium-22 starting with a solution containing 1 mol/l of nitric acid, 4 mol/l of $NaNO_3$, $^{137}Cs$ and $^{22}Na$ with a caesium-137 activity of 1558 kBq/l and a sodium-22 activity of 505 kBq/l.

To carry out the extraction, a device is used that is separated into two compartments by a supported liquid membrane, constituted by a microporous membrane made of polypropylene sold under the name CELGARD 2500 and which has the following characteristics:

Porosity factor: 0.45

Diameter of the pores: 0.04 μm.

Thickness of the membrane: 0.025 mm.

The pores of this membrane are filled with an organic phase constituted by nitrophenyl hexyl ether that includes 0.01 mol/l of the calixarene from Example 3.

The two compartments of the device are each fitted with a magnetic stirrer. The first compartment contains 55 ml of the aqueous starting solution and the second compartment contains an aqueous re-extraction solution consisting of water. The effective surface area of the membrane is 11.6 cm$^2$.

During this test, the activity of the aqueous starting solution from the first compartment is determined by γ spectrometry and the percentage of caesium-137 extracted into the second compartment is deduced from this.

Figure 4:
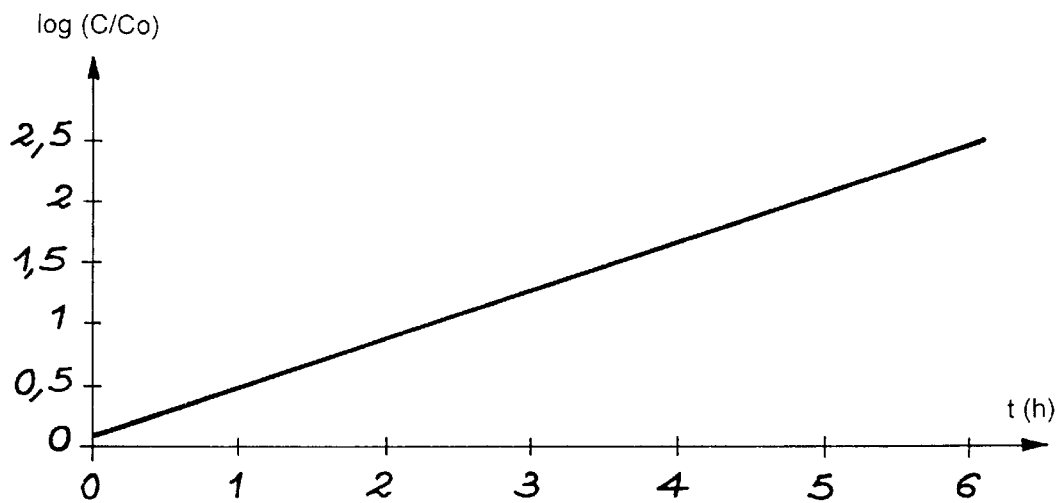
FIGS. 4 and 5 are graphs illustrating the change in the concentration of caesium in the starting solution as a function of time (in hours), during the extraction of caesium by a bis-crown calixarene (FIG. 4) and by a single crown calixarene (FIG. 5).

The results obtained are given in Table 2 and in FIG. 4.

This FIG. 4 represents the change in concentration of caesium in the re-extraction solution as a function of time (in hours).

The concentration of caesium is given in the y-co-ordinate by log (C/C$_0$) with C representing the concentration of caesium at time t and C$_0$ the initial concentration.

The transport corresponds to a permeability of the membrane to caesium-137 of 4.27 cm/h, that of sodium not being measurable; a permeability less than 0.1 cm/h.

EXAMPLE 9

Extraction of caesium-137

In this example, the same operating method is followed as in Example 8, using an aqueous starting solution containing 1 mol/l HNO$_3$, 4 mol/l of NaNO$_3$, $^{137}$Cs and $^{22}$Na with a caesium-137 activity of 1549 kBq/l and a sodium-22 activity of 505 kBq/l. In this case, the pores of the membrane are filled with an organic phase made up of nitrophenyl hexyl ether including 0.01 mol/l of the single crown calixarene from Example 1. The re-extraction solution is water, as in Example 8.

Figure 5:
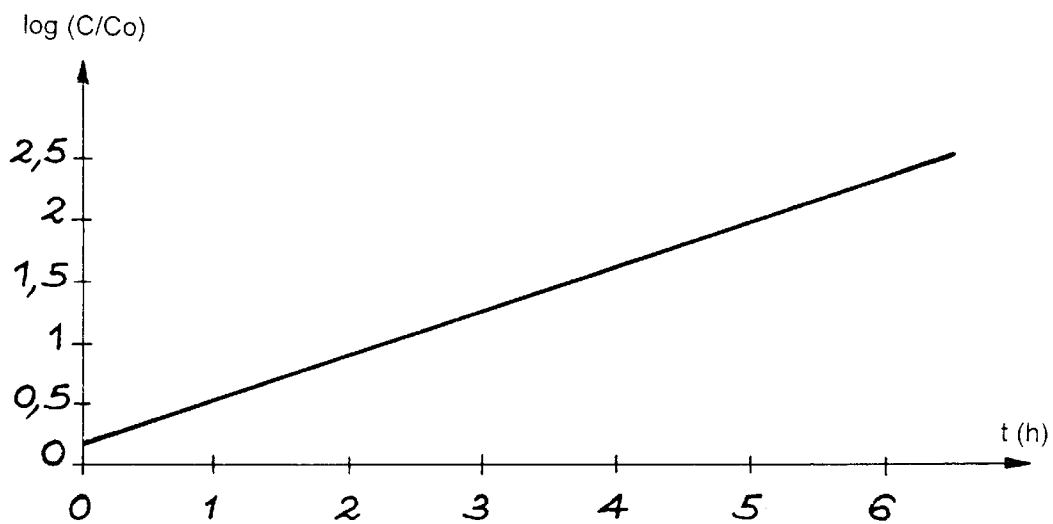

The results obtained are given in Table 3 and in FIG. 5.

FIG. 5 shows the change in the concentration of caesium (in log C/C$_0$) in the re-extraction solution as a function of time (in hours).

Under these conditions, the permeability of the membrane with respect to caesium-137 is 4.19 cm/h, that of sodium less than 0.1 cm/h.

TABLE 2

| Time (hours) | $^{137}$Cs activity in the aqueous starting solution (kBq/l) | $^{137}$Cs extracted (in %) |
| --- | --- | --- |
| 0 | 1558 | 0.0% |
| 0.5 | 1192 | 23.5% |
| 1 | 1057 | 32.2% |
| 1.5 | 827 | 46.9% |
| 2 | 685 | 56.0% |
| 2.5 | 569 | 63.5% |
| 3 | 481 | 69.1% |
| 3.5 | 367 | 76.4% |
| 4 | 297 | 80.9% |
| 4.5 | 242 | 84.5% |
| 5 | 208 | 86.6% |
| 5.5 | 180 | 88.4% |
| 6 | 134 | 91.4% |

TABLE 3

| Time (hours) | $^{137}$Cs activity in the aqueous starting solution (kBq/l) | $^{137}$Cs extracted (in %) |
| --- | --- | --- |
| 0 | 1549 | 0.0% |
| 0.5 | 1173 | 24.3% |
| 1 | 935 | 39.6% |
| 1.5 | 723 | 53.3% |
| 2 | 567 | 63.4% |
| 2.5 | 444 | 71.3% |
| 3.5 | 339 | 78.1% |
| 4.5 | 243 | 84.3% |
| 5 | 207 | 86.6% |
| 5.5 | 180 | 88.4% |
| 6 | 158 | 89.8% |
| 6.5 | 146 | 90.6% |

What is claimed is:

TABLE 1

| Calixarene Calixarene-bis-crown-6 | Examples 4 and 5 Cs(Na)NO$_3$ 5 × 10$^{-4}$M, HNO$_3$ 1M | | | Example 6 CsNO$_3$ 5 × 10$^{-4}$ M NaNO$_3$ 4M, HNO$_3$ 1M |
| --- | --- | --- | --- | --- |
| calixarene-bis-crown-6 | D$_{Cs}$ | D$_{Na}$ | D$_{Cs/Na}$ | D$_{Cs}$ |
| WO 94/12502 (Ex 3) Bis C6 | 19.5 | 1.3 × 10$^{-2}$ | 1500 | 10 |
| WO 94/12502 (EX 6b) Bis(1,2 Bz C6) | 32.5 | 1.7 × 10$^{-3}$ | 19000 | 20 |
| WO 94/12502 Bis(1,2 Np C6) | 29.5 | <10$^{-3}$ | >29500 | 8.1 |
| Invention (Ex 3) Bis (Di 1,2 Bz C6) | 31 | <10$^{-3}$ | >31000 | 56 |
| Calixarene-monocrown-6 | | | | |
| WO 94/24138 (Ex 3) Di propoxy C6 | 19.2 | 1.8 × 10$^{-3}$ | 10500 | 12 |
| WO 94/24138 (Ex 4) Di isopropoxy C6 | 28.5 | <10$^{-3}$ | >28500 | 18 |
| WO 94/24138 (Ex 6) Di octyloxy C6 | 33 | <10$^{-3}$ | >33000 | 25 |
| Invention (Ex 1) Dioctyloxy (Di 1,2 Bz C6) | 23 | <10$^{-3}$ | >23000 | 54 |

1. A crown calix-4-arene corresponding to the formula:

(I)

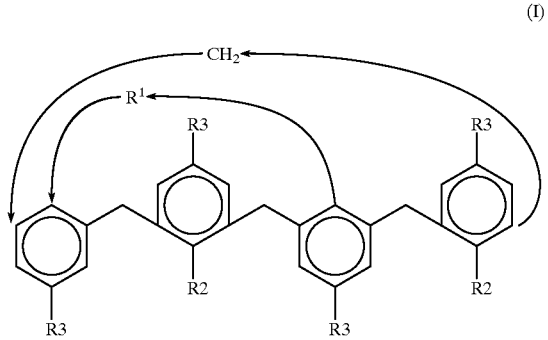

in which:

$R^1$ represents a group of formula:

where X and Y, which can be identical or different, represent an arylene or cycloalkylene group, m, n, p, r and s are whole numbers such that:

$m=s=1$, $1 \leq n \leq 3$, $p=0$ or $1$ $r=0$ or $1$, $R^2$ represents an OH group or an alkoxy group with from 1 to 18 carbon atoms, the two $R^2$ groups can be identical or different, or the two $R^2$ groups together form a group of formula:

in which) X, Y, m, n, p, r and s are as defined above; and $R^3$ represents a hydrogen atom or an alkyl group with 1 to 3 carbon atoms, with the condition that, in the case where the two $R^2$ groups together form a group of formula (II) p and r will not both be equal to 0 when n=1.

2. The crown calix-4-arene according to claim 1 corresponding to formula (I) with $R^2$ representing a OH group or an alkoxy group.

3. The crown calix-4-arene according to claim 2 in which $R^1$ represents the group of formula:

(III)

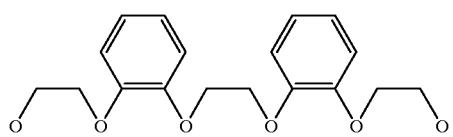

$R^2$ represents the octoxy group and $R^3$ represents a hydrogen atom.

4. The crown calix-4-arene according to claim 2 in which $R^1$ represents the group of formula:

(IV)

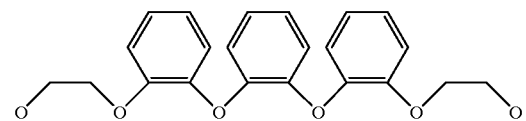

$R^2$ represents the octoxy group, and $R^3$ represents an atom of hydrogen.

5. The crown calix-4-arene according to claim 1 corresponding to formula (I) in which the two $R^2$ groups together form a group identical to $R^1$.

6. The crown calix-4-arene according to claim 5 in which $R^1$ represents the group of formula:

(III)

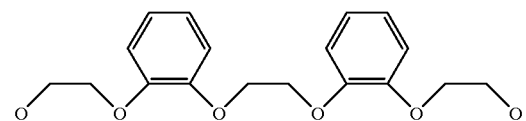

and $R^3$ represents a hydrogen atom.

7. The crown calix-4-arene according to claim 5 in which $R^1$ represents the group of formula:

(IV)

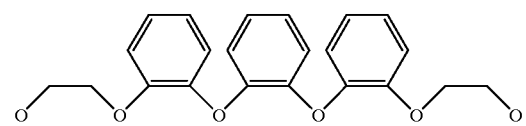

and $R^3$ represents an atom of hydrogen.

8. The crown calix-4-arene according to claim 1 in which $R^1$ represents the group of formula (III) or (IV):

(III)

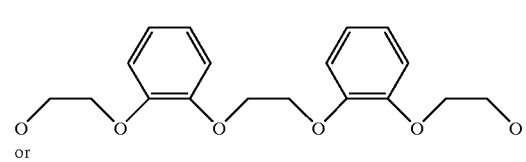

or (IV)

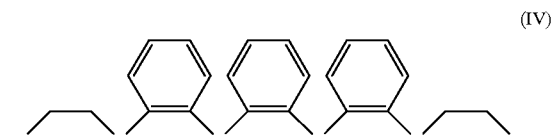

(III)

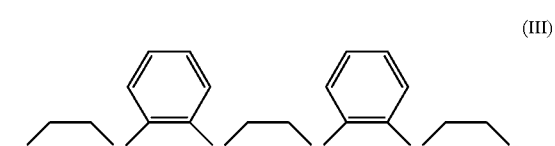

9. A method of preparation of a crown calix-4-arene corresponding to the formula:

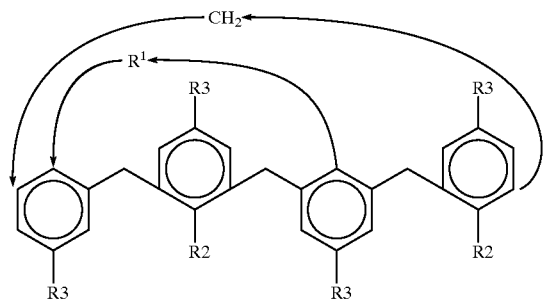

in which:

$R^1$ represents a group of formula:

where X and Y, which can be identical or different, represent an arylene or cycloalkylene groups, m, n, p, r and s are whole numbers such that:

=s=1,
$1 \leq n \leq 3$,
p=0 or 1
r=0 or 1, $R^2$ represents an OH group or an alkoxy group with from 1 to 18 carbon atoms, and $R^3$ represents a hydrogen atom or an alkyl group with 1 to 3 carbon atoms, comprised of reacting a calix-4-arene of formula:

(V)

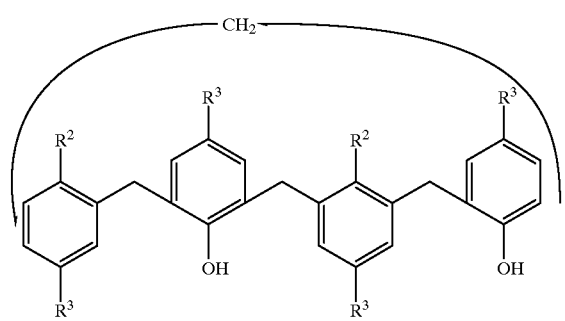

in which $R^2$ and $R^3$ have the meanings stated above, with a ditosylate of formula (VI):

(VI)

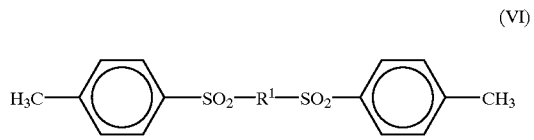

in which $R^1$ has the meaning stated above.

10. The method according to claim 9, in which $R^1$ being the group of formula:

(III)

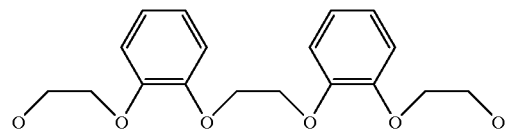

the tosylate be prepared by carrying out the following steps:

a) synthesis of 2-(2-hydroxyethoxy)phenol of formula:

(IX)

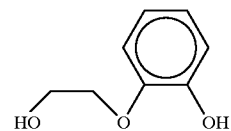

by reaction of catechol with ethylene carbonate b) reaction of the 2-(2-hydroxyethoxy)phenol obtained in a) with ethylene glycol ditosylate to obtain 1,2-bis[2-(2-hydroxyethoxy)phenoxyl]ethane and c) preparation of the tosylate by reaction of 1,2-bis[2-(2-hydroxyethoxy)phenoxy]ethane with tosyl chloride of formula:

(X)

11. The method according to claim 9 in which $R^1$ being the group of formula:

(III)

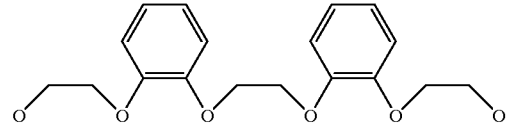

the tosylate is prepared by carrying out the following steps:

a) reaction of catechol with 2-chloroethanol to obtain 2-(2-hydroxyethoxy)phenol of formula:

(IX)

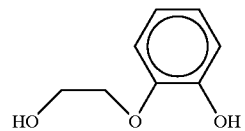

b) reaction of the 2-(2-hydroxyethoxy)phenol obtained in a) with 1,2-dibromethane to obtain 1,2-bis [2-(2-hydroxyethoxy)pbenoxy]etbane and c) preparation or the tosylate by reaction of 1,2-bis[2-(2-hydroxyethoxy)phenoxy]ethane with tosyl chloride of formula (X):

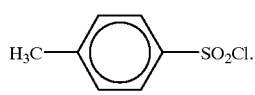
(X)

12. The method according to claim 9 $R^1$ being the group of formula:

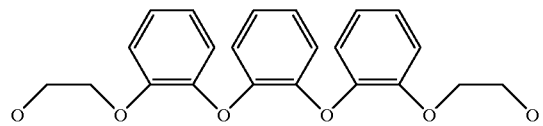
(IV)

the tosylate is prepared by carrying out the following steps:

a) preparation of the diphenol of formula:

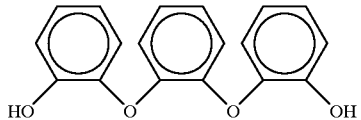
(XI)

b) reaction of the diphenol with ethylene glycol ditosylate.

13. The method according to claim 9 in which $R^1$ represents the group of formula:

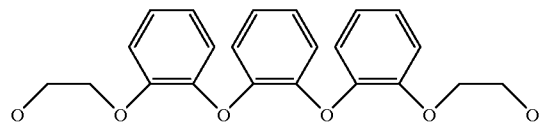
(IV)

the tosylate is prepared by carrying out the following steps:

a) preparation of the diphenol of formula:

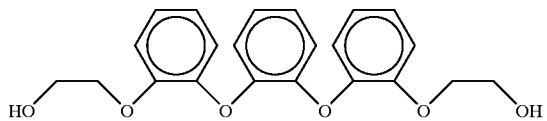
(XII)

b) reaction of the diphenol with tosyl chloride:

(X)

14. A method of preparing a calix-4-arene corresponding to the formula:

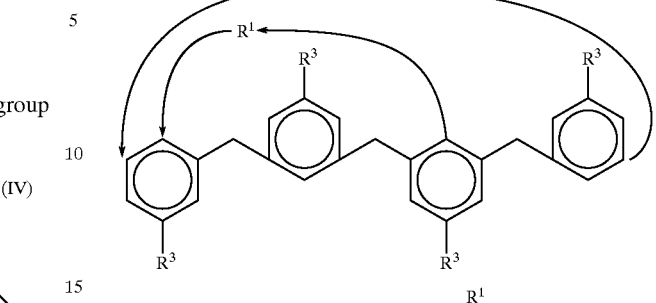
(Ia)

in which $R^1$ represents a group of formula:

$$O-(CH_2CH_2O)_m-(XO)_n-(CH_2CH_2O)_p-(YO)_r-(CH_2CH_2O)_s(II)$$

where X and Y, which can be identical or different, represent an arylene or cycloalkylene group, m, n, p, r and s are whole numbers such that:

m=s=1,
$1 \leq n \leq 3$
p=0 or 1
r=0 or 1, $R^3$ represents a hydrogen atom or an alkyl group with 1 to 3 carbon atoms, comprised of reacting calix-4-arene of formula:

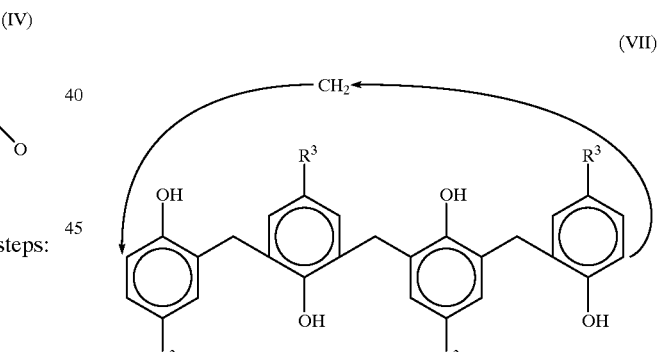
(VII)

with a ditosylate of formula:

(VI)

in which $R^1$ has the meaning stated above.

15. The method according to claim 14 in which $R^1$ being the group of formula:

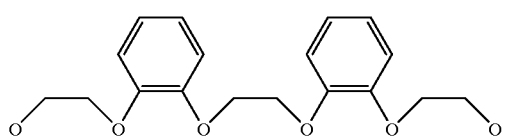
(III)

the tosylate is prepared by carrying out the following steps:

a) synthesis of 2-(2-hydroxyethoxy)phenol of formula:

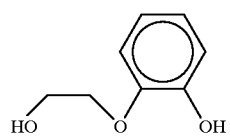
(IX)

by reaction of catechol with ethylene carbonate, b) reaction of the 2-(2-hydroxyethoxy)phenol obtained in a) with ethylene glycol ditosylate to obtain 1,2-bis[2-(2-hydroxyethoxy)phenoxy]ethane and c) preparation of the tosylate by reaction of 1,2bis[2-(2-hydroxyethoxy)phenoxy]ethane with tosyl chloride of formula:

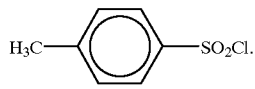
(X)

16. The method according to claim 14 in which $R^1$ being the group of formula:

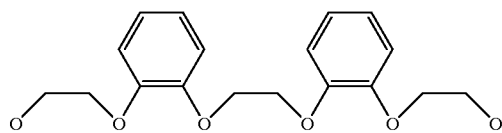
(III)

the tosylate is prepared by carrying out the following steps:

a) reaction of catechol with 2-chloroethanol to obtain 2-(2-hydroxyethoxy)phenol of formula:

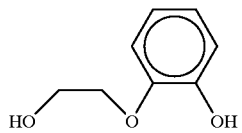
(IX)

b) reaction of the 2-(2-hydroxyethoxy)phenol obtained in a) with 1,2-dibromoethane to obtain 1,2-bis[2-(2-hydroxyethoxy)phenoxy]ethane and c) preparation of the tosylate by reaction of 1,2-bis[2-(2-hydroxyethoxy)phenoxy]ethane with tosyl chloride of formula (X):

(X)

17. The method according to claim 14 $R^1$ being the group of formula:

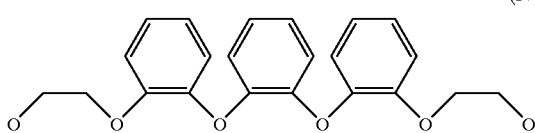
(IV)

the tosylate is prepared by carrying out the following steps:

a) preparation of the diphenol of formula:

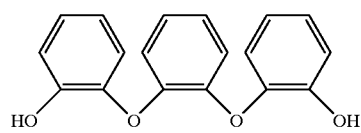
(XI)

b) reaction of the diphenol with ethylene glycol ditosylate.

18. A method according to claim 14 in which $R^1$ represents the group of formula:

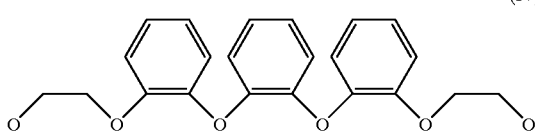
(IV)

the tosylate is prepared by carrying out the following steps:

a) preparation of the diphenol of formula:

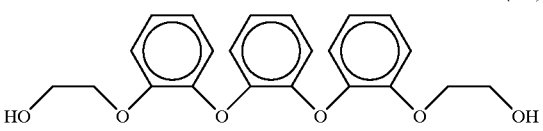
(XII)

b) reaction of the diphenol with tosyl chloride:

(X)

19. A method for the selective extraction of caesium from an aqueous solution that comprises of bringing this aqueous solution into contact with an immiscible liquid phase that includes a crown calix-4-arene corresponding to formula (I)

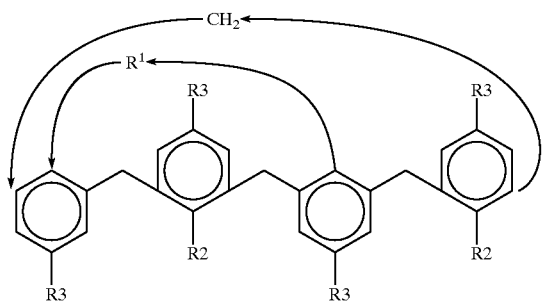

(I)

$R^1$ represents a group of formula:

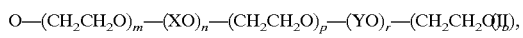

where X and Y, which can be identical or different, represent an arylene or cycloalkylene group, m, n, p, r and s are whole numbers such that:
m=s=1,
$1 \leq n \leq 3$,
p=0 or 1
r=0 or 1, $R^2$ represents an OH group or an alkoxy group with from 1 to 18 carbon atoms, the two $R^2$ groups can be identical or different, or the two $R^2$ groups together form a group of formula:

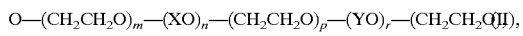

in which X, Y, m, n, p, r and s are as defined above; and $R^3$ represents a hydrogen atom or an alkyl group with 1 to 3 carbon atoms, with the condition that, in the case where the two $R^2$ groups together form a group of formula (II), p and r will not both be equal to 0 when n=1 separating the immiscible phase from the aqueous solution having extracted the caesium.

20. The method according to claim 19, in which the immiscible liquid phase is a solution of the crown calix-4-arene in an organic solvent.

21. The method according to claim 20, in which the organic solvent is a nitrophenyl alkyl ether.

22. The method according to claim 21, in which the aqueous re-extraction solution is distilled an de-ionised water.

23. The method according to claim 21, in which the immiscible liquid phase forms a liquid membrane, the aqueous solution containing the caesium is brought into contact with one surface of this membrane and the aqueous re-extraction solution is brought into contact with the opposite surface of this liquid membrane.

24. The method according to claim 20 in which afterwards, the caesium is recovered into an aqueous re-extraction solution by bringing the liquid phase which has extracted the caesium into contact with an aqueous solution.

25. The method according to claim 19, in which the aqueous starting solution is an aqueous effluent containing caesium with or without sodium arising from a spent nuclear fuel reprocessing plant.

26. The method according to claim 19, in which the calix-4-arene corresponds to formula (I) in which $R^1$ represents the group of formula:

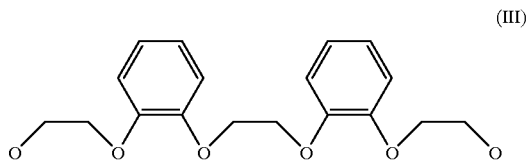

(III)

the two $R^2$ groups together form the group with formula (III) and $R^3$ represents a hydrogen atom.

27. The method according to claim 19, in which the calix-4-arene corresponds to formula (I) in which $R^1$ represents the group of formula:

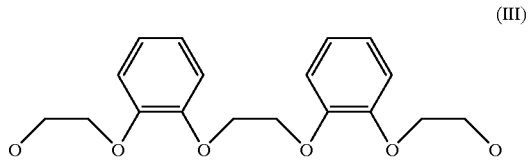

(III)

the two $R^2$ groups represent the octoxy group and $R^3$ represents a hydrogen atom.

* * * * *